US006797698B1

(12) United States Patent
Van Den Berghe

(10) Patent No.: US 6,797,698 B1
(45) Date of Patent: Sep. 28, 2004

(54) METHOD OF TREATING PROLONGED CRITICAL ILLNESS AND OTHER CONDITIONS HAVING A SIMILAR NEUROENDOCRINE PATTERN

(75) Inventor: Greta Herman Augusta Van Den Berghe, Leuven (BE)

(73) Assignee: K.U. Leuven Research & Development (BE)

( * ) Notice: Subject to any disclaimer, the term of this patent is extended or adjusted under 35 U.S.C. 154(b) by 0 days.

(21) Appl. No.: 09/146,205

(22) Filed: Sep. 2, 1998

(51) Int. Cl.[7] .................................................. A61K 38/06
(52) U.S. Cl. ............................ 514/18; 514/2; 514/12; 514/17; 530/324; 530/399
(58) Field of Search ............................. 514/18, 17, 2, 514/12; 530/324, 399

(56) References Cited

U.S. PATENT DOCUMENTS 5,492,916 A * 2/1996 Morriello et al. ........... 514/318

OTHER PUBLICATIONS

Remington: The Science and Practice of Parmacy, 19th ed. Vol., II, Gennaro, Editor MACK Publishing Co., Easton PA, 1952.*
Van Den Berghe et al. "Pituitary Responsineness to GH–Releasing Hormore, GH–Releasing Peptide—2 and Tyrotrophin–Releasing Hormone in Critical Illness", Clinc. Endocrinol., 43(3), 341–351, 1996.*
Brown et al. , "Frailty: constructing a common meaning, definition, and conceptual framework," International Journal of Rehabilitation Research, vol. 18, pp. 93–102 (1995).
Baxter, C. , "Circulating Levels and Molecular Distribution of the Acid–Labile (α) Subunit of the High Molecular Weight Insulin–Like Growth Factor–Binding Protein Complex," Journal of Clinical Endocrinology and Metabolism. vol. 70, No. 5., pp. 1347–1353.
Vanderschueren, D. et al., "Time–related increase of biochemical markers of bone turnover in androgen–deficient male rats," Bone and Mineral, vol. 26 (1994), pp. 123–131.
Mohan, Subburaman et al., "Development, Validation, and Application of a Radioimmunoassay for Insulin–Like Growth Factor Binding Protein–5 in Human Serum and Other Biological Fluids" Journal of Clinical Endocrinology and Metabolism, vol. 80, No. 9, pp. 2638–2645.

Honda, Yoko et al. "Recombinant Synthesis of Insulin–Like Growth Factor–Binding Protein–4 (IGFBP–4): Development, Validation, and Application of a Radioimmunoassay for IGFBP–4 in Human Serum and Other Biological Fluids," Journal of clinical Endocrinology and Metabolism, vol. 81, No. 4, pp. 1389–1396.
Baxter, Robert C. et al., "Radioimmunoassay of Growth Hormone–dependent Insulinlike Growth Factor Binding Protein in Human Plasma," J. Clin. Invest., vol. 78, Dec. 1986, pp. 1504–1512.
Baxter, Robert C. et al., "Two Immunoreactive Binding Proteins for Insulin–Like Growth Factors in Human Amniotic Fluid: Relationship to Fetal Maturity," Journal of Clinical Endocrinology and Metabolism, vol. 65, No. 3, pp. 423–431.
Knaus, William A. et al., "APACHE II: A severity of disease classification system," Critical Care Medicine, vol. 13, No. 10, pp. 818–829.
Gamrin, Lena, MD et al., "A descriptive study of skeletal muscle metabolism in critically ill patients: Free amino acids, energy–rich phosphates, protein, nucleic acids, fat, water, and electrolytes," Critical Care Medicine, vol. 24, No. 4, pp. 575–583, 1996.
Boonen, Steven, MD et al., "Relationship Between Baseline Insulin–Like Growth Factor–I (IGF–I) and Femoral Bone Density in Women Aged Over 70 Years; Potential Implications for the Prevention of Age–Related Bone Loss," JAGS, vol. 44, pp. 1301–1306, 1996.
Boonen, Steven et al., "Age–Related (Type II) Femoral Neck Osteoporosis in Men: Biochemical Evidence for Both Hypovitaminosis D– and Androgen Deficiency–Induced Bone Resorption," Journal of Bone and Mineral Research, vol. 12, No. 12, 1997, pp. 2119–2126.

* cited by examiner

Primary Examiner—Christopher S. F. Low
Assistant Examiner—David Lukton
(74) Attorney, Agent, or Firm—Webb Ziesenheim Logsdon Orkin & Hanson, P.C.

(57) ABSTRACT

A method of treating a subject suffering from a condition involving a blunted anterior pituitary hormone pattern in which Thyroid Releasing-Hormone (TRH) and Growth Hormone-Releasing Peptide (GHRP) are administered to the subject. The TRH and GHRP reactivate the blunted anterior pituitary hormone release mechanism of the subject. Treatable conditions include critical illness, non-coping mental and physical stress and frail elderly syndrome.

6 Claims, 9 Drawing Sheets

METHOD OF TREATING PROLONGED CRITICAL ILLNESS AND OTHER CONDITIONS HAVING A SIMILAR NEUROENDOCRINE PATTERN

FIELD OF THE INVENTION

The present invention relates to a new method of treating prolonged critical illness, non-coping stress, both physically and mentally, frail-elderly syndrome and other conditions involving a similar neuroendocrine pattern.

BACKGROUND OF THE INVENTION

Critically ill patients, supported with intensive care for weeks or months indifferently present a feeding-resistant "wasting syndrome", characterized by ongoing loss of protein whereas fat stores are paradoxically preserved or even built up. Consequences of this wasting are increased urea production related to muscle weakness, osteoporosis, deficient healing of wounds and fractures and impaired recovery of failing organ systems, together further prolonging the dependency on expensive intensive care support.

The present inventor were the first to establish that, from a neuroendocrine perspective, the chronic phase of intensive care-supported severe illness is different from the acute post-resuscitation phase. Immediately after onset of acute illness or trauma, anterior pituitary function is activated, which is thought to contribute to the metabolic adaptation essential for survival. It has always been assumed that the neuroendocrine pattern found during the acute phase is similar to the one found during the chronic stages of critical illness. In contrast however, the chronic phase of protracted critical illness is characterized by a uniformly suppressed pulsatile secretion of growth hormone (GH), thyrotropin (TSH) and prolactin (PRL), related to low serum levels of ICF I IGFBP-3, acid-labile subunit (ALS), thyroid hormones and leptin.

The present inventor found that the relative impairment of pulsatile GH and TSH release is due to a reduced content or activity of hypothalamic TRH and of the putative endogenous ligand for the GH-secretagogue receptor.

It was therefore hypothesized by the present inventor that the impaired hypothalamic and anterior pituitary hormone secretion, as it occurs distinctively in the chronic phase of critical illness, contributes to the development and maintenance of the wasting syndrome. The inventor assumed that the wasting syndrome is caused by an increase in catabolism due to impaired pulsatile TSH secretion and a shortage of thyroid hormones and a simultaneous disruption of the anabolism due to a decrease in pulsatile growth hormone secretion and GH-dependent IGF's and IGFBP's.

It was found that pulsatile secretion of GH and TSH during protracted critical illness-can be reactivated by the continuous and combined infusion of the GH-secretagogue GHRP-2 and TRH for 21–45 h, which elicits a proportionate rise in circulating IGF-I, IGFBP-3, ALS, leptin and thyroid hormones without altering serum cortisol levels.

In the research that led to the present invention this mechanism was further explored by extending the infusion time of GHRP-2+TRH to 5 days which allows a first limited evaluation of metabolic effectiveness of this novel endocrine strategy.

This led the present inventor to conclude that infusion of GHRP-2+TRH for 5 days in protracted critical illness reactivated the blunted GH and TSH secretion, with preserved peripheral responsiveness and feedback inhibition and without affecting serum cortisol. Concomitantly, a reversible shift towards anabolic metabolism (reduced catabolism and increased anabolism) was induced, as indicated by biochemical markers. Hereby, the first evidence of effectiveness of GHRP-2+TRH for treatment of the "wasting syndrome" in protracted critical illness was provided.

In more general terms it was concluded that simultaneous administration of a GHRP together with TRH is capable of correcting the secretion of growth hormone and TSH after which the endogenous feed-back systems are again capable of normalizing both the level of growth hormone and TSH secreted and the peripheral effects that occur as a reaction on the activity of growth hormone and TSH. Thus, the anabolism is improved and the increased catabolism is reduced.

As an alternative, in conditions involving impairment of only one axis administration of only one of the two compounds can be used for treatment.

SUMMARY OF THE INVENTION

Based on these observations, the present invention provides a method of treating protracted critical illness by administering to a subject suffering from the illness an amount of Thyroid Releasing Hormone (TRH) and of Growth Hormone-Releasing Peptide (GHRP) suitable to reactivate the blunted anterior pituitary hormone release mechanism.

More in general, the invention relates to, methods of treating conditions which involve a blunted anterior pituitary hormone release pattern, comprising the administration to a subject, suffering from a condition involving the blunted anterior pituitary hormone pattern, of an amount of Thyroid Releasing Hormone (TRH) and of Growth Hormone-Releasing Peptide (GHRP) suitable to reactivate the blunted anterior pituitary hormone release mechanism. Such conditions are for example critical illness, non-coping mental and physical stress and the frail-elderly syndrome. These conditions are further defined in Brown., I. et al., International Journal of Rehabilitation Research 18, 93–102 (1995)

The invention further relates to a therapeutical composition containing GHRP and TRH in an amount and ratio sufficient to be suitable to reactivate the blunted anterior pituitary hormone release mechanism.

DETAILED DESCRIPTION OF THE INVENTION

The present invention can be used for the treatment of the wasting syndrome that is found in patients suffering from protracted critical illness. However, the treatment of the invention can also be used for indications that involve a related blunting of the anterior pituitary release mechanism. This is based on the observation that various other conditions are thought to involve a neuroendocrine pattern that is similar to the one found in chronic illness. Such conditions are for example non-coping stress, both physical and mental, and the so-called frail-elderly syndrome, which is found in some but not all aging people and is for example characterized by a tendency to break bones such as hips etc. The invention thus also applies to methods of treating these types of conditions.

Optionally the administration of GHRP and TRH can be supplemented with Luteinizing Hormone Releasing Hormone (LHRH). A shortage of pulsatile LH secretion can lead to testosterone deficiency in males, which in turn can cause an increase in catabolism. It has been found that LHRH alone has no effect, but in combination with TRH and/or GHRP it is found to be effective in lowering catabolism, which is the result of a testosterone deficiency.

The term "GHRP" as used in this application is intended to encompass every protein or peptide or non-peptide analogue that is capable of binding to the Growth Hormone-Releasing Peptide-Receptor. Although an endogenous ligand for this receptor has not yet been identified, various artificial ligands have been designed that are capable of binding to the receptor. Examples of these are "MK-0677" and others.

This application refers to "simultaneous application of GHRP and TRH". However, this phrase is not intended to limit the invention to cases in which GHRP and TRH are actually administered at the same time. Rather, the invention also relates to situations in which only one of two anterior pituitary axes is suppressed (e.g. TRH for only blunted TSH secretion and GHRP for only blunted GH secretion).

The present invention further relates to therapeutical compositions comprising GHRP and TRH in an amount and ratio sufficient to be suitable to reactivate the blunted anterior pituitary hormone release mechanism. Such amounts can for example vary between 0.01 and 10 µg/kg/h for GHRP and 0.01 and 10 µg/kg/h for TRH when given by infusion. Other administration forms can require other amounts. The ratio between the two varies for example between 0.5 and 4, more in particular between 0.5 and 2. In addition, in particular for the treatment of male patients such therapeutic composition can be supplemented with a suitable amount of LHRH to eliminate the effects of testosterone deficiency. LHRH can also be used with either TRH or GHRP alone.

In the Example that follows, metabolic effectiveness of the releasing peptides in the wasting condition associated with protracted critical illness was assessed by studying biochemical markers of catabolism such as urea production and urinary excretion of collagen crosslinks and markers of anabolism such as serum concentrations of osteocalcin and leptin.

Fourteen patients (68±11y), critically ill for 40±28 days, were studied for 10 days. Blood was sampled overnight every 20 minutes on night 0, 5 and 10 and daily at 06:00 h. 24 h urine was collected in HCl. After a first nocturnal profile, patients received 5 days placebo and 5 days GHRP-2+TRH (1+1 µg/kg/h), in a random order. Serum concentrations of GH, IGF-I, IGFBP-1, IGFBP-3, ALS, IGFBP4, IGFBP-5, insulin, cortisol, TSH, T4, T3, rT3, prolactin (PRL), osteocalcin (OC), urea, creatinine as well as deoxypyridinoline/creatinine in 24 h urine (DPD) were determined. Pulsatile GH secretion was quantified by deconvolution analysis, It was then found that at baseline, mean nocturnal GH concentrations (mean±SD 1.04±0.69 µg/L, median 0.75 µg/L) and GH pulse amplitude (0.10±0.11 µg/Lv/min, median 0.05 µg/Lv/min) were related to low serum IGF I (87±8 µg/L), IGFBP-3 (1.41±0.21 mg/L) and ALS (6.45±0.88 mg/L). Serum concentrations of IGFBP-1 (10.8±6.5 µg/L) related inversely to serum IGFBP-3; insulin (36±36 µIU/mL) related positively to ALS. Nocturnal TSH (1.30±1.33 mIU/L, median 0.89 mIU/L) and PRL (10.0±3.2 µg/L) levels were low-normal, in the presence of low T3 (0.85±0.24 nmol/L) and T4 (77±25 nmol/L) and elevated cortisol (424±49 nmol/L). Levels of OC (29.5±14.3 ng/mL), a biochemical marker of bone formation, and of the stimulatory IGFBP-5 (379±124 µg/L) were reduced in relation to the suppressed GH-IGF(BP)-axis, whereas markers of catabolism such as DPD (106±80 nmol/-mmol) and urea/creatinine ratio (UCR: 84±39) as well as the inhibitory IGFBP-4 (877±204 [µg/L) were all elevated, related positively to IGFBP-1 and inversely to thyroid hormone concentrations. Serum leptin levels (15.8±13.1 µg/L, median 10.8 µg/L) were related to the GH dependent IGF(BP)'s and to bone turnover (OC and DPD).

Placebo infusion during the first 5 days decreased or did not alter the studied parameters. After days GHRP-2+TRH infusion, pulsatile GH secretion, TSH and PRL levels were (still) elevated. Within 2 days, IGF-1, IGFBP-3, ALS, IGFBP-5, leptin, T4 and T3 had increased to (near) normal levels and UCR had decreased with a mean 17%, further remaining stable until day 5. Five days GHRP-2+TRH increased OC by 19±7% vs. −6±5% with placebo (P=0.03) and reversed the spontaneous IGFBP-1 rise. Infusing placebo following GHRP2+TRH infusion returned all hormonal levels to pretreatment values, except IGFBP-3 and IGFBP-5, which remained slightly higher, and allowed UCR to rise again. Reverse T3, cortisal, IGFBP-4 and DPD were unaltered

DESCRIPTION OF THE FIGURES

In the example reference is made to the following figures and tables.

Figure 1:
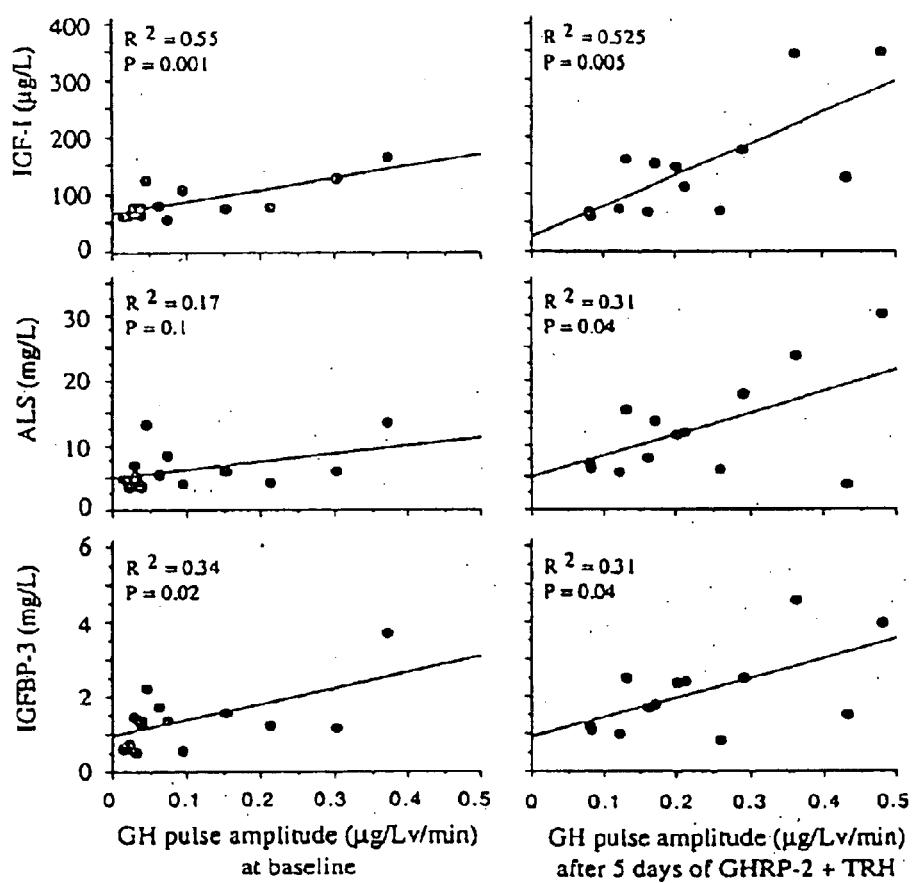
FIG. 1: At baseline as well as after 5 days infusion with GHRP-2+TRH (1+1 µg/kg/h), GH pulse amplitude was related to circulating levels of IGF-I, IGFBP-3 and ALS in protracted critical illness.

Table 1: Clinical patient data are depicted. Both randomization groups were comparable. Randomization group, age (years), gender, BMI (kg/m2), diagnosis (AA=abdominal aneurysm, CABG=complicated coronary artery bypass grafts, LCOS=low cardiac output syndrome), Apache II score 24 h after admission on intensive care, Apache II at study inclusion, the concomitant administration of exogenous insulin, type of feeding (TPN total parenteral nutrition; PN+EN=parenteral and enteral nutrition; EN=full enteral nutrition), number of days on the ICU at inclusion, total ICU stay (days), outcome.

Table 2: Endocrine and metabolic measurements at baseline. For a number of parameters, the study group was compared with an age- and gender-matched sample of 65 community-living control subjects (15 women, 50 men) that were selected from a group of subjects recruited for an independent study (Boonen et. al., J. Am. Geriatr. Soc. 44: 1301–1306 (1996) and J. Bone Miner. Res. 12: 2119–2126 (1997)) that had been studied with the same assays. For these selective parameters, mean±SD of the matched controls and the P-value for comparison are also presented.

EXAMPLE

1. Methods

1.1 Patients and Concomitant Treatment

As it has been shown that protein wasting during prolonged critical illness is determined by the duration of the ICU stay and not by the underlying disease (Gamrin et al., Crit. Care Med. 24, 575–583 (1996)), patients depending on intensive care (including mechanical ventilatory support) for at least two weeks and with an expected stay in the intensive care unit (ICU) for at least another two weeks were eligible for participation in this study. Further inclusion criteria were a stable condition without dopamine treatment for at least 72 h, this in view of the pronounced suppressive effect dopamine exerts on pituitary function in this type of patients.

Exclusion criteria were age below 18 years, preexisting neurologic, psychiatric, metabolic or endocrine disease; intracranial lesions; important liver failure (prothrombin time less than 30%); renal failure requiring replacement therapy; concomitant treatment with glucocorticoids, estrogens, somatostatin, thyroid hormones, $Ca^{2+}$-reentry blockers, clonidine, amiodarone, ctomidate, dopamine agonists or antagonists and the use of iodine in antiseptic dressings or as IV contrast agents.

A total of 14 patients (4 women, 10 men) were included (Table 1). The mean±SD age was 68±11 years (range 44–81 years). Apache II score, an indicator of severity of illness with higher values reflecting a more critical condition (Knaus et al., Crit. Care Med. 13, 818–829 (1985)), was 15.5±6.4 (range 7–33) on the ICU-admission day and 14.1±4.1 (range 8–23) on the day of inclusion in the study. Body mans index (BMT) was 24.5±4.6 kg/m2 (range 19–38 kg/m2).

Patients were critically ill for 40±28 (range 14–92) days at the time of inclusion in the study. Concomitant treatment included standardized, continuously administered feeding: either total parenteral nutrition (n=8), combined parenteral and enteral nutrition (n3) or full enteral feeding (n=3). Caloric intake (a mean of 29 non-protein Cal/kg/d, range 23–35 Cal/kg/d) and composition (0.8–1.6 g/kg amino acids per day, 2.8–4.0 g/kg glucose per day, 1–1.5 g/kg fat per day covering 25–40% of non-protein calories) were adequate. Other concomitant therapies were standardized vitamin supplements including 220 IU cholecalciferol per day (n=14); inotropic support with exogenous non-dopaminergic catecholamines (n=4); antibiotics (n=10); analgesia and sedation with continuously infused opioids (n10) and/or benzodiazepines (n=3).

Blood glucose levels were monitored every 4 h and targeted between 5 and 9 mmol/L with continuous insulin infusion if necessary (n=8) (Mizock, Am. J. Med. 98, 75–84 (1999)). At study start, blood glucose levels were 7.5±1.3 mmol/L (range 4.9–8.6 mmol/L). Human albumin was continuously infused when serum levels were very low (mean serum albumin concentration at inclusion was 2.5±0.4 g/dL). The mean serum level of triglycerides was 159±70 mg/dL (range 54–278 mg/dL) and C-Reactive Protein concentration was elevated (136±8 mg/L). Continuous hemodynamic monitoring always included ECG, intra-arterial blood pressure, central venous pressure, core and peripheral temperature. During the entire study period, the concomitant ICU-therapy, including the feeding regimen, remained virtually unaltered, allowing for optimization of, and eventually weaning off ventilatory and hemodynamic support.

The ultimate outcome of the studied patients was a total ICU stay of 69±40 (range 23–146) days. One patient died from intercurrent sepsis during the course of the study (on day 5 of GHRP-2+TRH infusion). Three patients died on ICU, respectively 35, 27 and 11 days after inclusion in the study. Ten patients were discharged to the ward, left the hospital subsequently and are known to be well 4–9 months after study end. The observed mortality in this study (28%) was not significantly different from the expected mortality (37%), as determined in a group of patients, matched for age ($\geq 44$ years), duration of stay on ICU ($\geq 21$ days) and underlying diseases (n=111) treated on the ICU during the 12 months preceding the study start.

1.2 Study Design and Peptide Administration

Patients were studied during a total time span of 10 days, and received an overnight (21:00 h to 0:06 h) sampling (every 20 min) on night 0, night 5 and night 10. Additional blood samples were taken daily at 06:00 h. In 7 of the 14 patients, a complete 24 h urine collection was obtained on day 0, 5 and 10.

Patients were randomized into one of two cross-over study groups:

1. group 1 (n=6) received placebo for 5 days after the first night profile, followed by a 1+1 µg/kg/h continuous infusion of GHRP-2+TRH (1+1 µg/kg bolus at 06:00 h, followed by a 1+1 µg/kg/h continuous infusion) for the next 5 days.
2. group 2 (n=8) received GHRP-2+TRH (1+1 µg/kg bolus at 06:00 h, followed by a 1+1 µg/kg/h continuous infusion) for 5 days followed by placebo for the next five days.

Placebo (NaCl 0.9%), TRH (200 μg/mL NaCl 0.9%, Ferring, Kiel, Germany) and GHRP-2 (50 μg/mL NaCl 0.9%, Kaken Pharmaceutical Co., Ltd., Tokyo, Japan) infusions were given through a separate lumen of a central venous catheter, inserted for clinical purposes. A PERFUSOR secura FT pump with a 50 ml PERFUSOR syringe (B. Braun, Melsungen, Germany) permitted precise infusions of small volumes at a constant rate. Inadvertent interruption of the infusion or unanticipated bolus injections of the peptides are thereby avoided.

Serum concentrations of GH, TSH and PRL were measured in each sample of the nocturnal time series and serum cortisol levels were measured every hour. At 21:00 h of night 0, 5 and 10, serum 1GF-I and IGF binding protein (IGFBP)-1 was determined. Daily at 06:00 h, serum concentrations of IGF-I, IGFBP-1, IGFBP-3, the acid-labile subunit (ALS), IGFBP-4, IGFBP-5, insulin, leptin, thyroxine (T4), triiodothyronine (T3), reverse T3 (rT3) and 25 (OH)D3 were determined.

Serum concentrations of osteocalcin (OC), type I procollagen (PICP), bone-specific alkaline phosphatase (sALP) were determined at 21:00 h and 06:00 h on study night 0 and 5.

Urinary excretion of 3-hydroxypyridinium crosslinks of collagen [pyridinoline and deoxy-pyridinoline normalized for urinary creatinine in an acidified (HCl) 24 h urine collection (PYD and DPD)] was determined when a complete urine collection was available (n=7).

Serum concentration of urea normalized for serum concentration of creatinine (UCR) was determined at 06:00 h on a daily clinical basis.

1.3 Blood Sampling

All blood samples were collected through an arterial line inserted for clinical purposes independently of this study. The Edwards VAMP™ system (Baxter Healthcare Corporation, Irvine, Calif., USA) was used, permitting withdrawal of undiluted blood samples from an indwelling catheter, without undue blood lose. The total amount of blood sampled per patient over 10 days was 270 mL. Blood was collected into Vacutainer® tubes; after clotting and centrifugation, the serum was kept frozen at −20° C. until assay.

1.4 Assays

All samples of each patient were processed in the same assay run.

For selected parameters, the study group was compared with an age- and gender-matched sample of 65 community-living control subjects (15 women, 50 men) previously recruited and studied with the same assays for an independent study (Boonen et. al. J. Am. Geriatr. Soc. 44: 1301–1306 (1996) and J. Bone Miner. Res. 12: 2119–2126 (1997)).

The serum concentrations of GH in all profiles were measured by RIA, using the Nichols Institute Diagnostics HGH immunoassay 100T kit (40–2155). The intra-assay coefficient of variation was 4.2% at 1.4 μg/L and 2.8% at 12.2 μg/L. The detection limit was 0.02 μg/L.

The plasma concentrations of total IGF-I were measured by RIA, after acid-ethanol extraction. The intra-assay coefficient of variation was 10.1% at 95 μg/L and 5.5% at 474 μg/L. The between assay coefficient of variation was 14.8% at 109 μg/L and 10.1% at 389 μg/L. The detection limit was 10 μg/L. Normal range in healthy adults is 100–300 μg/L. Age and gender-matched control subjects presented with a mean±SD IGF-I concentration of 130±47 μg/L.

IGFBP-1 was purified from amniotic fluid as described by Baxter et al. (Baxter et al, J. Clin. Endocrinol. Metab. 65: 423–431 (1987)) using an IGF-I affinity column. The measurements were done by RIA, using $^{125}$I-labeled IGFBP-1 as radio label (specific activity 284mCi/mg) and a rabbit polyclonal antiserum. The detection limit was 25 pg per tube. The intra-assay coefficient of variation ranged from 2.4 to 4.0% (n–10 for 6 samples), and the inter-assay coefficient of variation ranged from 6.2 to 9.7% (for 2 samples, n=15 and 14, respectively). Normal values for a gender-matched control population (n=114, aged between 18–60 years) were 11.6+9.0 μg/L, ranging from 0 to 52.4 μg/L.

The serum IGFBP-3 concentrations were measured by RIA as previously described (Baxter & Martin, J. Clin. Invest. 78, 1504–1512 (1986)), using antiserum R-100. The intra-assay coefficient of variation was 6.2% at 2.5 mg/L and 5.5% at 5.7 mg/L, and the between assay coefficient of variation was 11.9% at 2.9 mg/L and 14.5% at 6.3 mg/L. Normal ranges are 2.2 to 4.6 mg/L.

The serum ALS concentrations were assessed by RIA, as described elsewhere (Baxter J. Clin. Endocrin. Metab. 70, 1347–1353 (1990)). The intra-assay coefficient of variation was 3.4%, and the between assay coefficient of variation was 10.5% at 5.3 mg/L and 5.4% at 24 mg/L. Normal ranges are 17–34 mg/L.

Circulating levels of IGFBP-4 were measured by RIA using recombinant human IGFBP-4 as antigen, tracer and standard (Honda et al., J. Clin. Endocrinol. Metab. 81, 1389–1396 (1996)). Age and gender-matched control subjects presented with a mean±SD IGFBP-4 concentration of 607±165 ng/mL.

IGFBP-5 was measured by RIA using guinea pig antisera made against recombinant IGFBP-5 (Mohan et al., J. Clin. Endocrinol. Metab. 80, 2638–2645 (1995)). Human recombinant IGFBP-5 was used as standard and tracer. The intra- and interassay coefficients of variations were less then 4% and 8% respectively. Age and gender-matched control subjects presented with a mean±SD IGFBP-5 concentration of 612±119 ng/mL.

The serum insulin levels were determined by a human insulin IRMA (Medgenix INS-IRMA, Biocource, Fleurus, Belgium). The detection limit was 1 μIU/mL. The intra assay coefficient of variation was 4.5% at 6.6 μIU/mL and 2.1% at 53 μIU/mL.

The serum leptin concentrations were determined by a human leptin RIA (Linco Research, St. Charles, Mo., USA). The detection limit was 0.5 μg/L. The intra assay coefficient of variation was 6.3% at a leptin concentration of 15.6 μg/L.

The serum concentrations of TSH were measured by immunoradiometric assay using the TSH Riabead II (Abbott Laboratories, North Chicago, USA). The intra-assay coefficient of variation was 4.3% at 1.2 mIU/L and 2.2% at 7.0 mIU/L. The detection limit was less than 0.02 mIU/L. Normal nocturnal values range from 0.15–7 mIU/L.

The serum concentrations of T4 were measured by RIA using the Tetrabead-125 Diagnostic Kit (Abbott Laboratories, North Chicago, USA). The intra-assay coefficient of variation was 4.6% at 59 nmol/L and 4.4% at 102 nmol/L. Normal values range from 71–154 nmol/L.

The serum concentrations of T3 were measured by RIA using the T3 Riabead Kit (Abbott Laboratories, North Chicago, USA). The intra-assay coefficient of variation was 5.9% at 1.1 nmol/L and 4.4% at 2.8 nmol/L. Normal values range from 1.2–2.9 nmol/L.

The serum concentrations of rT3 were measured by RIA using the rT3 Kit (Techland SA, Liege, Belgium). The intra-assay coefficient of variation was 10.5% at 0.8 nmol/L and 10.3% at 4 nmol/L. Normal values range from 0.3–0.8 nmol/L.

The serum concentrations of PRL were measured by immunoradiometric assay using the PRL-IRMA Kit (Medgenix, Fleurus, Belgium). The intra assay coefficient of variation was 6.2% at 6.6μg/L and 4.7% at 46.4 μg/L. The detection limit was 2.9 μg/L. Daytime normal levels for men are ≦9.9 μg/L; for females in the reproductive period ≦19.7 μg/L; elderly women ≦8 μg/L and old men ≦4.9 μg/L. Sleep-associated nocturnal PRL concentrations range between 9 and 25 μg/L.

The serum concentrations of cortisol were measured by RIA after extraction with dichloromethane. The intra assay coefficient of variation was 3.1 % at 417 nmol/L. Normal ranges are 276–607 nmol/L at 8 am; 0–276 nmol/L at 8 pm and <50 nmol/L at midnight if asleep.

Osteocalcin was measured by a homologous human osteocalcin RIA. The sensitivity was 2 μg/L, and the between assay variation coefficient was 7%). Age and gender-matched control subjects presented with a mean±SD OC of 35±29 μg/L.

Serum PICP was measured by RIA (Orion Diagnostica, Espoo, Finland). The sensitivity was 1.2 μg/L. The between assay variation coefficient was 6.6% at 216 μg/L and 4.0% at 435 μg/L. The within assay coefficient of variation was 2.71% at 214 μg/L and 3.2% at 451 μg/L. Normal values range between 50–170 μg/L for women and 38–202 μg/L for men. Matched control subjects presented with a mean±SD PICP of 51.4±20.4 μg/L.

Serum sALP was determined by immunoradiometric assay (Tandem-R Ostase®, Hybritech Inc., San Diego, Calif. 92121. USA). The detection limit was 2.0 μg/L. The intra assay CV was 6.7% at 13.2 μg/L and the inter assay CV was 8.1 1 at 11.7 μg/L. Normal values range between 7 and 23 μg/L. Matched control subjects presented with a mean±SD sALP of 9.1±5.4 μg/L.

Urinary pyridinolines (PYD and DPD) were measured in 24 h urine collections acidified with hydrochloric acid (Vanderschueren et al., Bone Miner. 26, 123–131 (1994)). A 0.5 ml aliquot of urine was hydrolyzed with 0.5 ml of 12M of hydrochloric acid and applied to a CF-I cellulose column (Whatman, Maidstone, Kent, UK) according to the method of Black and colleagues (ref Black and Robin). The cross linking amino acids were eluted with heptafluorobutyric acid and water (0.1%), separated by centrifugation and the lower layer containing the cross links was carefully removed. Samples were subjected to high-pressure liquid chromatography analysis (Zorbax SB-CI8, 3.5 μm, 4.6x150 mm, Rockland Technologies, Newport, Del.) and fluorescence detection. Samples were quantified by external standardization (courtesy of S. Robins). Values were expressed as nmol/mmol creatinine and urinary creatinine was measured calorimetrically (Heinegard). Interassay coefficients of variation were 11.5% and 13.3% for PYD and DPD respectively (n=12). Matched control subjects presented with a mean±SD PYD concentration of 62±27 nmol/mmol and a mean±SD DPD of 12±5 nmol/mmol.

Serum 25 (OH) D3 was measured by competitive binding assay as previously described (Bouillon). Normal values for age matched community living males are 18.7±7.3 μg/L and 27.5±15.6 μg/L in age matched community living women. Matched control subjects presented with a mean±SD 25 (OH)D3 concentration of 20.1±9.0 μg/L.

Urea concentration was measured in serum on a routine clinical basis using a kinetic UV test (Boehringer Mannheim Systems, Germany/Hitachi 737). Normal values range from 20–45 mg/dL. The total impression was 3.15% at 50 mg/dL and 1.76% at 158 mg/dL. Creatinine concentration was measured daily in serum using a Jaffé method (Boehringer Mannheim Systems, Germany/Hitachi 737). Normal values range from 0,7–1.35 mg/dL. The total impression was 3% at 1.9 mg/dL and 1.5% at 4.1 mg/dL. The normal values for UCR range from 15–40.

1.5 Data Analysis

The time series of sequential serum GH concentrations measured overnight were transformed into pituitary secretion profiles by eliminating the effect of metabolic clearance, using multiple parameter deconvolution analysis (Veldhuis & Johnson, Methods Enzyrnol. 210, 539–575 (1992)). This method is designed to compute hormonal half-life and the number, amplitude and mass of underlying pituitary secretory bursts and to estimate tonic (basal or non-pulsatile) secretion (Veldhuis, supra).

Individual GH half-lifes were determined in each of the three study nights and averaged before application to the data series. Besides mean serum concentrations, the following parameters were calculated for each hormonal profile in each subject: basal secretion rate (estimated as the amount of hormone that should be continuously released from the pituitary in order to achieve serum concentrations approximating the mean of the lowest 5% of all values observed (μg per Lv (Liter of distribution volume) and per min); amplitudes (maximal secretory rate (μg per Lv and per min) and temporal positions of all secretory bursts; the mass of hormone secreted per burst (estimated as the area of the resolved secretion burst (μg per Lv); and the mean pulsatile production (calculated as the product of the number of secretory bursts and the mean secretory burst mass over the time interval considered (μg per Lv over 9 h). The proportion of pulsatile secretion (%) was calculated as the pulsatile production divided by the sum of the pulsatile and basal production, each expressed as μg per Lv over 9 h), multiplied by 100. The total GH production (μg/Lv per 9 h) was calculated as the sum of pulsatile GH production (μg/Lv over 9 h) and basal GH secretion (μh/Lv.min×560 min).

TSH, PRL and cortisol profiles were quantified by determining area under the curve (AUC), calculated using the trapezoid rule, and by mean nocturnal serum concentration.

At inclusion, groups were compared using two-tailed unpaired t-test, Mann-Whitney U-test and Chi-square test. Comparison with literature reference values for pulsatile fraction of growth hormone release was performed using the two tailed, one sample t-test. Effect of intervention was analyzed using repeated measures analysis of variance (ANOVA) or two-tailed paired t-test, as appropriate. Results are expressed as mean±SD unless indicated otherwise.

2. Results

Baseline patient characteristics are shown in tables 1 and 2 and were identical in both study groups. The releasing peptides were well tolerated. No side effects were noted, apart from an increased insulin requirement to maintain blood glucose level below the preset upper limit of 9 mmol/L in those patients already receiving exogenous insulin infusion (Table 1). Serum concentrations of triglycerides did not change significantly throughout the study.

I. SOXHTOTROPIC AXIS

Baseline values for GH secretion and IGF-1 and its binding proteins are shown in Table 2 and were similar in both study groups.

The fraction of GH released in a pulsatile fashion (63±14%, median 58%) was low (P<0.0001) compared to the normal 99% in the presence of low-normal mean nocturnal serum GH concentration (1.04±0.69 μg/L), the latter found to correlate positively with mean nocturnal serum IGF-I concentration (87±32 μg/L; $R^2$=0.29, P=0.04). This was due to the positive correlation of serum IGF-I with pulsatile GH production ($R^2=0.41$, P=0.01), GH pulse amplitude ($R^2=0.55$, P=0.002) (FIG. 1) and, to a lesser extent, basal (non-pulsatile) GH release ($R^2$ 0.35, P=0.02). GH pulse amplitude also correlated positively with low IGFBP-3 ($R^2=0.34$, P=25 0.03).

Figure 2:
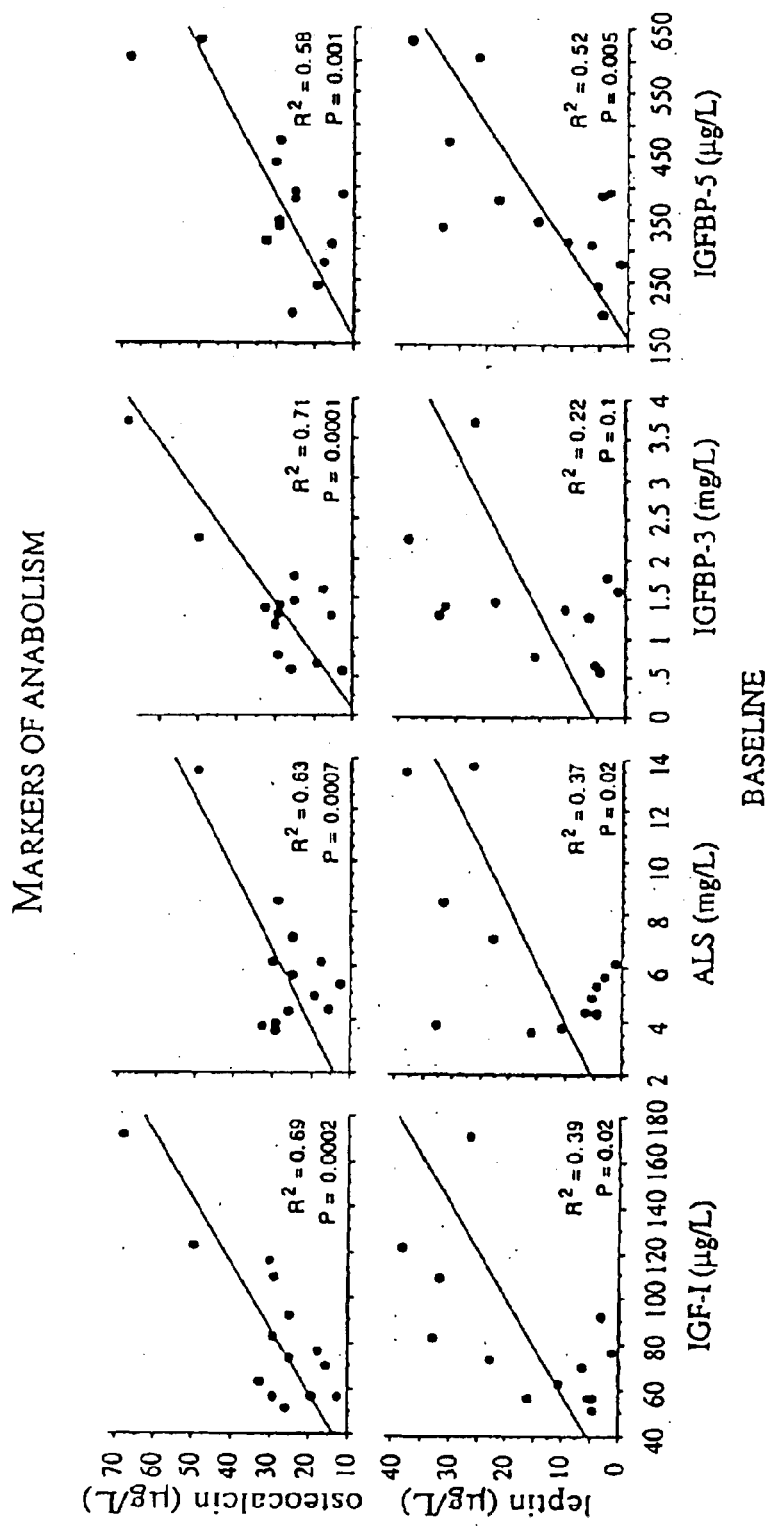
FIG. 2: At baseline, markers of anabolism during protracted critical illness, such as serum concentration of osteocalcin and leptin, were positively correlated with serum levels of the GH-dependent IGF-I and IGF-binding proteins.

Morning serum IGF-I concentration (85±33 µg/L) was low compared to matched controls (130±47 µg/L, P=0.001) and positively correlated with low IGFBP 3 ($R^2=0.78$, P<0.0001) and ALS ($R^2=0.73$, P=0.0001) (FIG. 2). Serum levels of IGFBP-3 ($R^2=0,78$, P<0.0001 and ALS ($R^2=0.73$, P=0.000) (FIG. 2) Serum levels of IGFBP-1 correlated inversely with IGFBP-3 ($R^2=0.33$, P=0.03) but not significantly with IGF-I ($R^2=0.25$, P=0.07).

Figure 3:
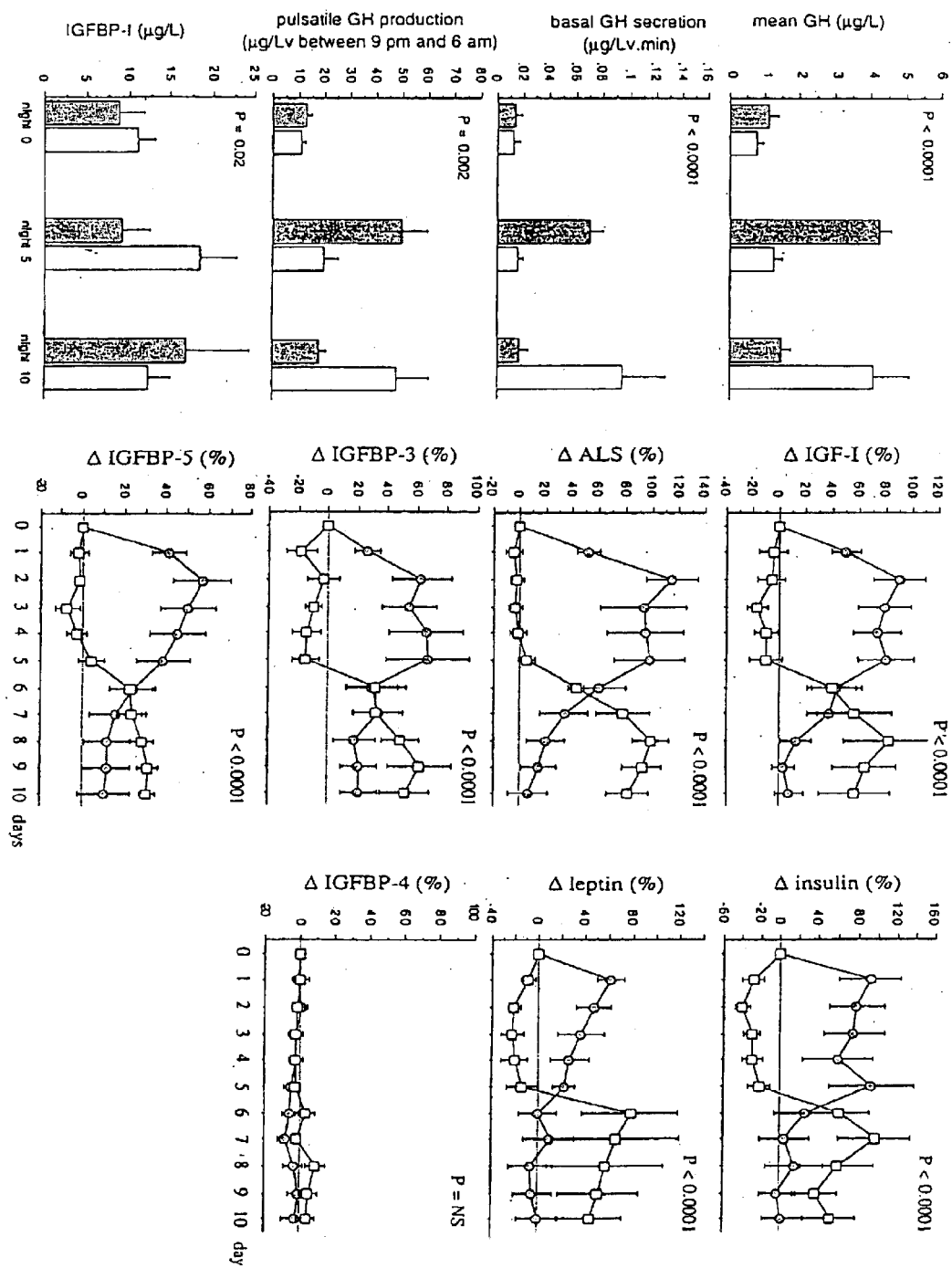
FIG. 3: The responses to a randomized treatment with either five days GHR-P-2+TRH infusion (1+1 µg/kg/h) followed by 5 days placebo (filled symbols) or 5 days placebo followed by five days GHRP-2+TRH infusion (1+1 µg/kg/h) (open symbols) of deconvolution-derived GH secretion and of serum levels of IGF-1, IGFBP-1, IGFBP-3, ALS, IGFBP-4, IGFBP-5, insulin and leptin are depicted.

The changes observed in GH secretion and in levels of IGF-I and its binding proteins during infusion of placebo and GHRP-2+TRH are presented in FIG. 3. After 5 days of continuous GHRP-2+TRH infusion, mean GH concentration, basal (non-pulsatile) GH secretion, GH pulse amplitude and pulsatile GH production were (still) elevated in both groups, respectively a mean 3.3-fold, 5.4-fold, 3-fold and 3.3-fold higher than pretreatment values, again decreasing after 5 days of subsequent placebo in group 2.

Placebo infusion during the first 5 days decreased or did not alter serum levels of IGF-1, IGFBP-3, and ALS. In both groups, infusion of GHRP-2+TRH evoked an immediate rise in IGF-1, ALS and IGFBP-3, reaching a maximum after 2 to 3 days. Thereafter, serum concentrations of IGF-I, ALS and IGFBP-3 remained stable at normal or near-normal levels until day 5. Five days of placebo following GHRP-2+TRH infusion returned IGF-I and ALS levels to pretreatment values, whereas IGFBP-3 remained slightly elevated. Infusion of GHRP-2+TRH appeared to counteract a spontaneous increase in serum IGFBP-1 concentration during placebo.

II. INSULIN

Baseline fed-state insulin levels are shown in Table 2. Insulin concentration was comparable in both groups and independent of whether or not patients needed exogenous insulin infusion in order to keep blood glucose level below the preset value of 9.0 mmol/L. Serum insulin concentration was unrelated to GH secretion, IGF-1, IGFBP-1 and IGFBP-3 levels whereas it correlated positively with serum ALS concentration ($R^2=0.28$; P=0.05).

Placebo infusion during the first 5 days decreased or did not alter serum insulin concentration (FIG. 3) In both groups, infusion of GHRP-2+TR4 evoked an immediate rise in insulin, reaching a maximum within 1 to 2 days, after which it remained stable until day 5. Five days of placebo following GHRP-2+TRH infusion returned insulin levels to pretreatment values within 2 days.

III. LEPTIN

Baseline leptin levels are shown in Table 2. Leptin concentrations were similar in both groups, and appeared independent of BMI, age, caloric intake, C-reactive protein, serum cortisol level or thyroid status. In contrast, baseline leptin concentrations did correlate positively with serum insulin ($R^2=0.41$, P=0.02), IGF-I ($R^2=0.38$, P=0.02) and ALS ($R^2=0.37$, P=0.03) concentrations.

Placebo infusion allowed serum leptin concentrations to further decrease (FIG. 3). In both groups, infusion of GHRP-2+TRH evoked a rise in leptin concentrations, reaching a maximum within 1 day. Five days of placebo following GHRP-2+TRH infusion returned leptin levels to pretreatment values within 1 day.

After 1 day of GHRP-2+TRH infusion, concentrations of leptin correlated positively with insulin ($R^2=0.49$, P=0.008) and IGF-I ($R^2 0.36$, P=0.03). This relationship was maintained after 5 days of infusion with GHRP-2+TRH ($R^2$ 0.42, P=0.02 and $R^2=0.36$, P=0.03 respectively for insulin and IGF-1).

IV. TRYROID AXIS

Table 2 shows baseline thyroid status which was similar in both study groups. At baseline, serum concentrations of T4 correlated inversely with serum levels of IGFBP-1 ($R^2=0.27$; P=0.05) and serum concentrations of T3 tended to follow that inverse correlation ($R^2=0.20$; P=0.1).

Figure 4:
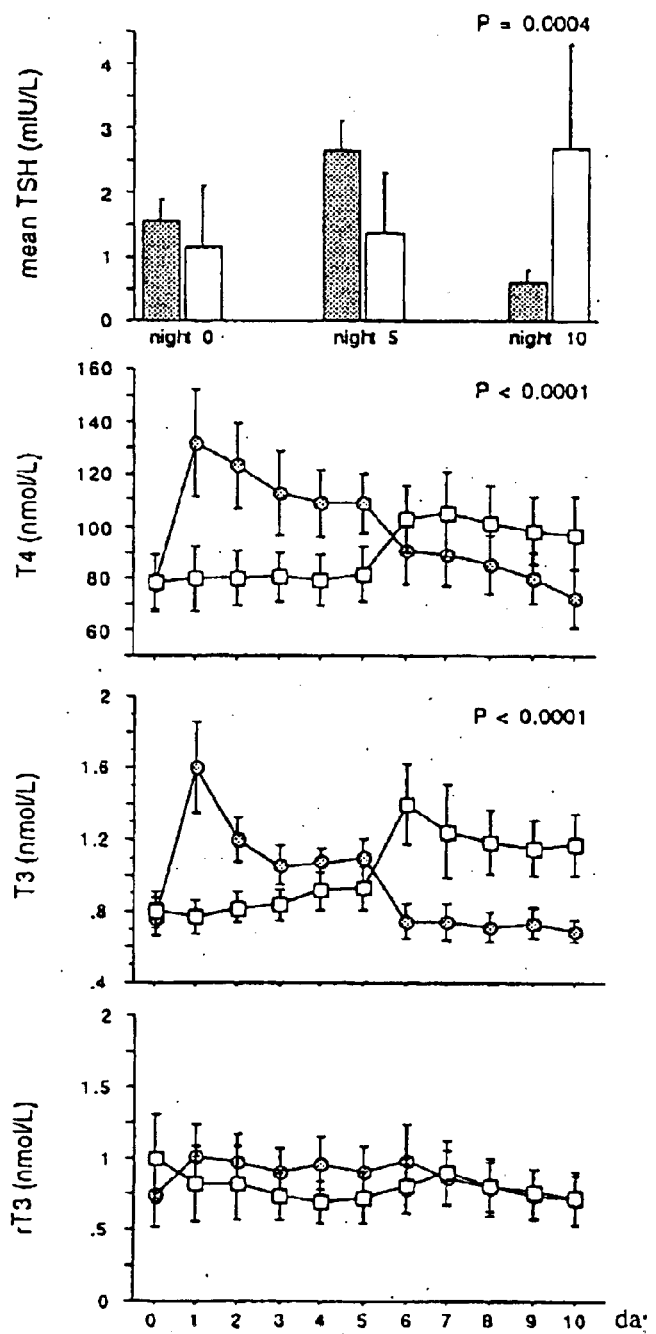
FIG. 4: The responses to a randomized treatment with either five days GHRP-2+TRH infusion (1+1 µg/kg/h) followed by 5 days placebo (filled symbols) or 5 days placebo followed by five days CHRP-2+TRH infusion (1+1 µg/kg/h) (open symbols) of mean nocturnal TSH concentrations and of serum levels of T4, T3 and rT3 are shown.

During infusion of placebo in group 1, there was no significant change in mean nocturnal TSH concentration. After 5 days of GHRP-2+TRH infusion mean nocturnal TSH was (still) twice the pretreatment value in both groups, whereas it decreased below the pretreatment level after five subsequent days on placebo in group 2 (FIG. 4).

During infusion of placebo in group 1, T4 levels remained unaltered. Upon treatment with CHRP2+TRH there was an immediate rise in circulating T4, reaching a plateau after 2 or 3 days in both groups. During five days on subsequent placebo in group 2, T4 levels decreased again to values not significantly different from pretreatment levels.

Comparable changes were documented for circulating T3 levels. Five days after GHRP 2+TRH interruption, T3 levels were not different from pretreatment levels.

Only one group revealed a minute but significant increase of rT3 during GHRP-2+TRH infusion. These changes were not reproducible in the other randomization group and represented less than twice the variation coefficient of the assay and therefore considered not to be clinically relevant. Five days after GHRP-2+TRH interruption, rT3 levels were not different from pretreatment levels.

V. PRL

During infusion of placebo in group 1, mean nocturnal PRL levels slightly decreased from 11.1±1.9 µg/L to 9.0±1.9 µg/L. Upon treatment with GHRP-2+TRH, PRL levels increased in both groups (from 9.0±1.9 µg/L to 13.1±5.7 µg/L and from 9.0±3.9 µg/L to 16.2±15.5 µg/L respectively), and after 5 subsequent days of placebo infusion in group 2, PRL concentrations decreased again to 9.5±6.9 µg/L. (P=0.001 with ANOVA)

VI. CORTISOL

Nocturnal cortisol levels were elevated (Table 2) but did not appear to be linked to any of the other studied endocrine and metabolic parameters Nocturnal serum cortisol levels were not detectably altered by the infusion of either placebo or GHRP-2+TRH in both groups (data not shown).

VII. UREA PRODUCTION (UCR)

Figure 5:
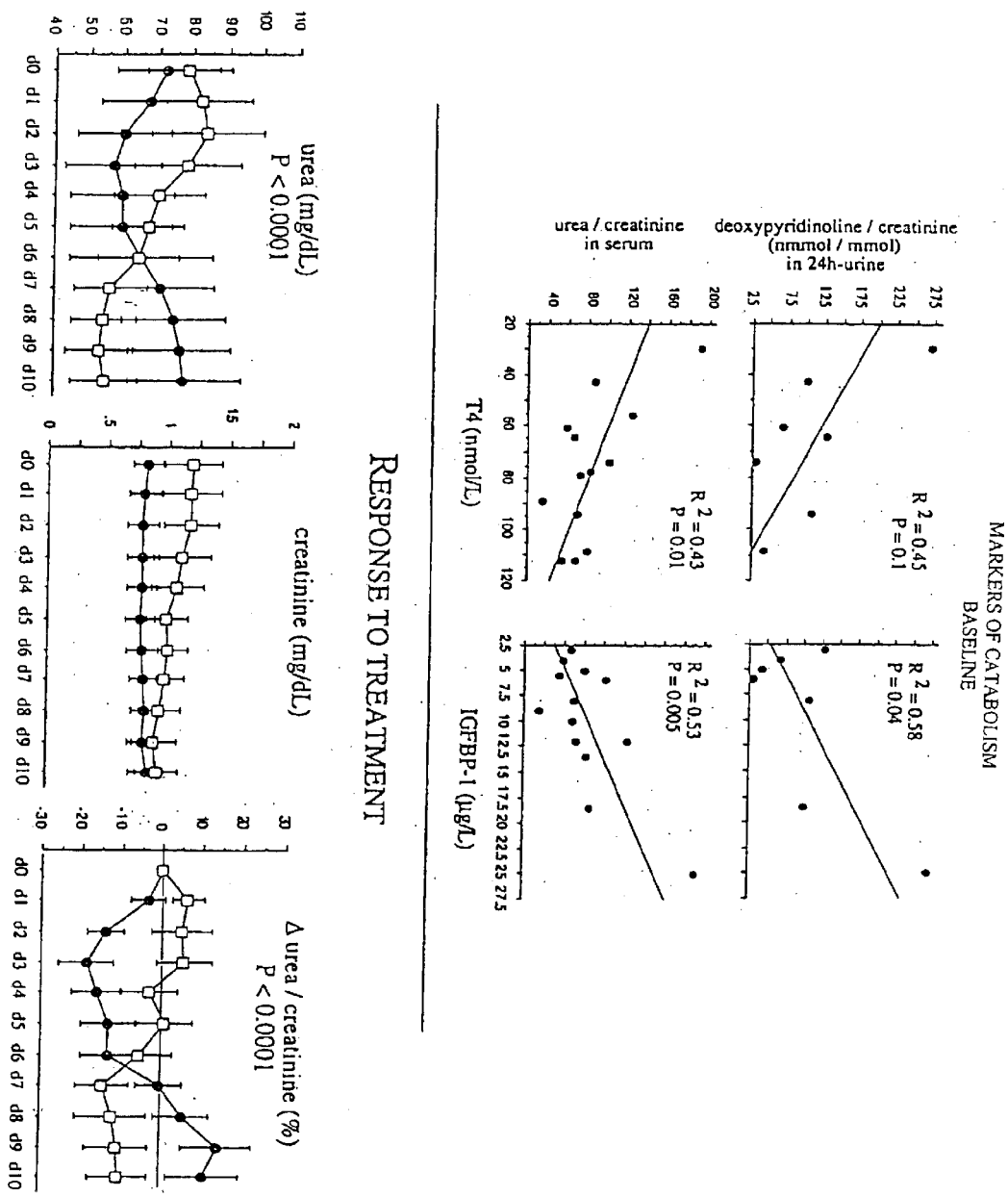
FIG. 5: Low levels of T4 and high levels of 1GFBP-1 at baseline are associated with increased markers of protein hypercatabolism such as high urea/creatinine ratio and increased urinary excretion of deoxy-pyridinoline (DPD). The response in urea production to a randomized treatment with either five days GHRP-2+TRH infusion (1+1 µg/kg/h) followed by 5 days placebo (filled symbols) or 5 days placebo followed by five days GHRP-2+TRH infusion (1+1 µg/kg/h) (open symbols) are depicted, indicating limitation of protein hypercatabolism upon treatment.

At baseline, the high UCR (mean±SD 84±39), indicating increased protein catabolism, was inversely correlated with serum concentrations of T4 ($R^2=0.43$, P=0.01) and positively related to serum IGFBP-1 levels ($R^2=0.53$, P=0.005) (FIG. 5) but independent of the somatotropic axis or serum cortisol. The first 5 days on placebo infusion did not significantly alter UCR 5). In both groups, infusion of GHRP-2+TRH evoked a drop in UCR (a mean−19% and −15% respectively) which became significant from day 2 onward. Five days of placebo following GHRP-2+TRH infusion allowed UCR to rise again.

After 5 days of treatment, the UCR remained inversely correlated with circulating levels of thyroid hormones ($R^2=0.27$, P=0.06 for T4 and $R^2=0.37$, P=0.02 for T3) and positively with 1GFBP-1 ($R^2=0.56$, P=0.005).

VIII. BONE TURNOVER, VITAMIN D AND BONE-RELATED IGFBP'S

In the patients, from whom a 24 h urine collection on HCl was available, DPD in 24 h urine, an indicator of osteoclast activity, was found to be substantially elevated (Table 2:

more than 10-fold the normal values), and to be positively correlated and with leptin concentrations ($R^2=0.73$, P=0.01), with mean nocturnal levels of IGFBP-1($R^2=0.58$, P=0.04) (FIG. 5) with UCR ($R^2=0.61$, P=0.03) and inversely with T3 ($R^2=0.52$, P=0.06). The same trend of inverse correlation between DPD and serum T4 levels ($R^2=0.45$, P=0.1) (FIG. 5) was documented. DPD was independent of serum cortisol.

Serum levels of PICP (n=13) were elevated at baseline and independent of DPD and PYD. Serum sALP levels (n=14) were normal (table 2) and independent of DPD and PYD.

Serum OC levels (n=14) were lower then those observed in the matched control group (P=0.04), as were serum concentrations of IGFBP-5 (P<0.0001) whereas levels of IGFBP-4 were higher (P<0.0001) (n=14) (Table 2). Serum OC levels were found to correlate positively with circulating levels of IGF-I ($R^2=0.69$, P=0.0002), ALS ($R^2=0.63$, P=0.0007), IGFBP-3 ($R^2=0.71$, P=0.0001), IGFBP-5 ($R^2=0.58$, P=0.001) (FIG. 2) and to a lesser extent with serum leptin concentrations ($R^2=0.40$, P=0.02), whereas they were independent of DPD in 24 h urine (FIG. 6), thyroid status and serum cortisol levels.

Figure 6:
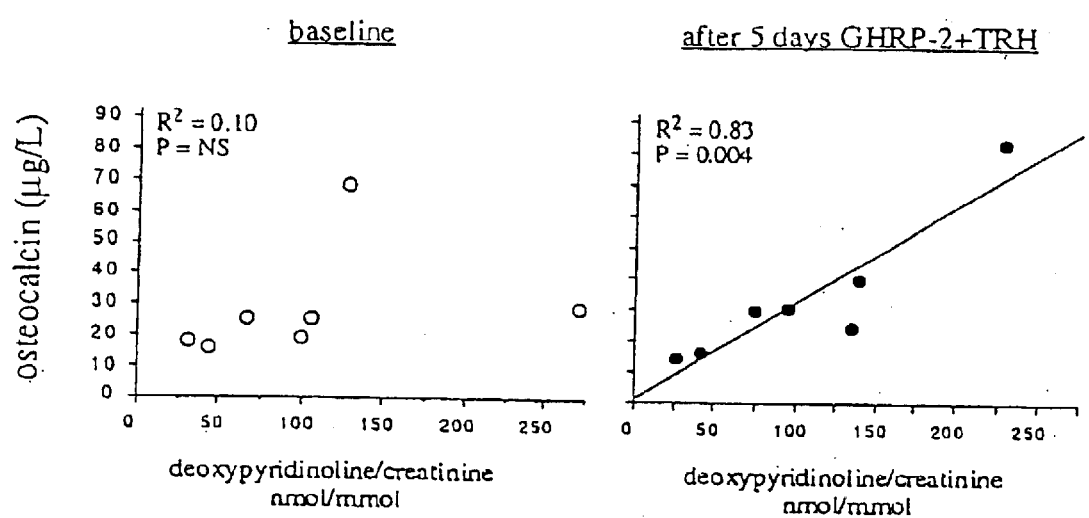
FIG. 6: Absent correlation between relatively low serum concentrations of osteocalcin and elevated urinary excretion of deoxypyridinoline (DPD) at baseline suggests uncoupling between osteoblasts and osteoclasts, and was reinstalled after 5 days treatment with GHRP-2+TRH.
Figure 7:
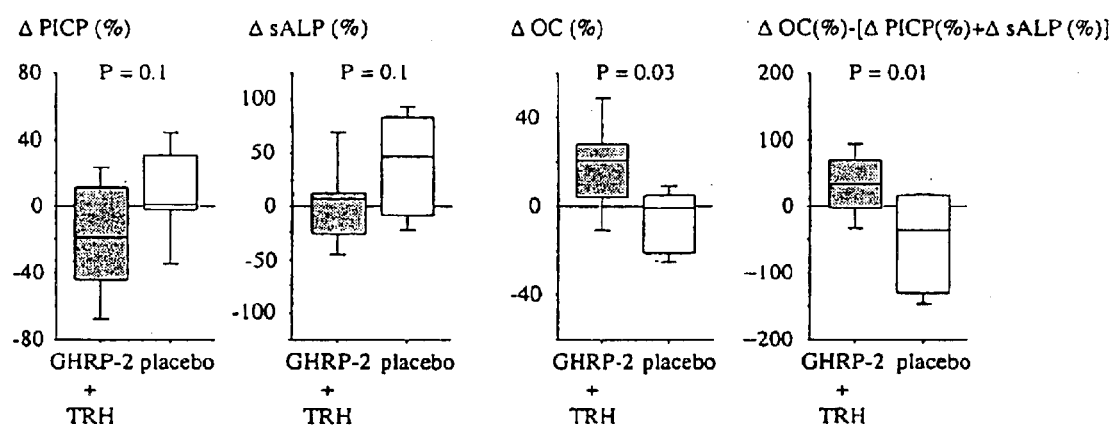
FIG. 7: At random assignment to start with 5 days GHRP-2+TRH (1+1 µg/kg/h) infusion or 5 days placebo, showed that after 5 days, GHRP-2+TRH treatment had increased serum OC concentrations, whereas it did not significantly alter, but had a tendency to decrease, concentrations of PICP and sALP. Box plots represent medians, P25-P75 and PI0-P90.

Urinary excretion of DPD and serum IGFBP-4 levels were not significantly altered by either placebo or GHRP-2+TRH infusion. In contrast, OC was increased with a mean 19% after 5 days GHRP2+TRH infusion compared to −5.5% with placebo (P=0.03) (FIG. 7). The changes in serum IGFBP-5 concentration mimicked those in IGF-1, ALS and IGFBP-3 (FIG. 3). Five days infusion of GHRP2+TRH restored the positive correlation between OC and DPD ($R^2=0.83$, P=0.004) (FIG. 6). The decrease in PICP and in sALP after 5 days GHRP-2+TRE infusion did not reach significance (P=0.1) (FIG. 7) However, Δ%OC-(Δ%PICP+Δ%sALP), an indicator of shift towards more activity in mature osteoblasts, increased with a mean 34% versus a mean decrease of −52% with placebo (P=0.01) (FIG. 7). Moreover, after 5 days of secretagogue infusion, OC remained positively correlated with serum levels of IGF-I ($R^2=0.60$, P=0.002) and leptin ($R^2=0.49$, P=0.008), and DPD remained positively correlated with circulating levels of leptin ($R^2=0.61$, P=0.04).

At baseline, and despite a daily cholecalciferol supplement of 220 IU, serum levels of 25-OH-D3 were relatively low for the age (11±5 μg/L) (Table 2) but unrelated to any of the above mentioned parameters. 25-OH-D3 levels were not detectably altered by the infusion of either placebo or GHRP2+TRH in both groups (data not shown).

IX. ENDOCRINE CHANGES IN RELATION TO OUTCOME

Figure 8:
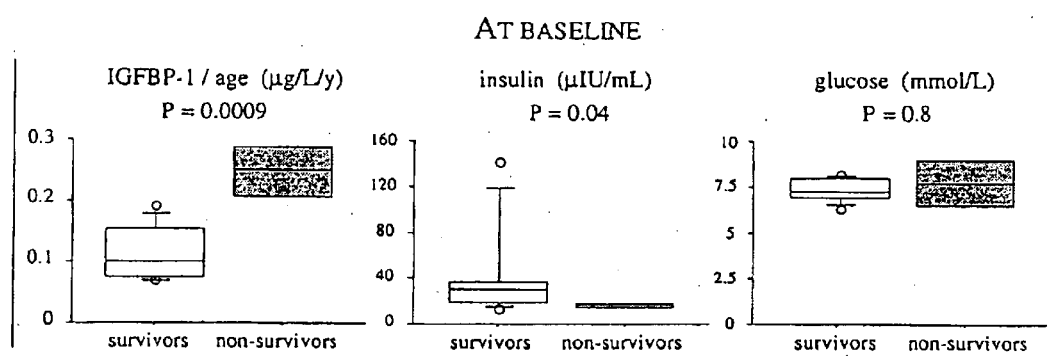
FIG. 8: At baseline, IGFBP-1 concentration for age was higher in the non-survivors (n=4) compared to survivors (n=10), a value of 0.2 µg/L/y being discriminative. Concomitantly, serum insulin levels were lower for the same blood glucose level in the non-survivors. Box plots represent medians, P25–P75 and P10–P90 and circles represent the absolute values for outliers.

At study inclusion, survivors and non-survivors were only distinguishable by age (mean±SD respectively 65±11 y versus 78±3 y, P=0.04), IGFBP-1 levels (respectively 7.35±3.8 μg/L versus 16.08±3,12 μg/L, P=5 0.002)—both variables being interrelated ($R^2=0.39$, P=0.01)—and serum insulin concentrations (44.5±41 μIU/mL, versus 16±3 μIU/mL, P=0.04), whereas blood glucose levels were comparable (7.4±0.8 mmol/L versus 7.6±2.2 mmol/L, P=0.8) (FIG. 8). Even after correction for age, high 1GFBP-1 levels remained predictive for fatal outcome (P=0.0009), with a cut-off value of 2.0 μg/L per year being discriminative. In contrast, Apache II scores, with higher values indicating more severe illness, calculated either at the time of admission to ICU or at study inclusion, could not predict the ultimate outcome.

Figure 9:
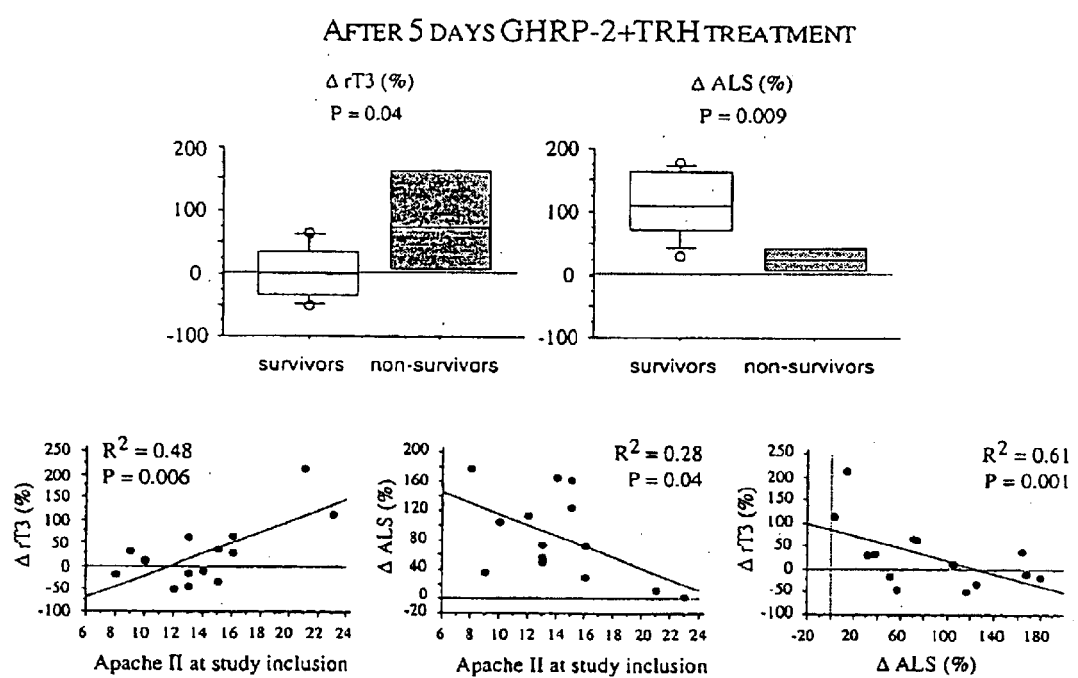
FIG. 9: Non-survivors (n4) presented with a lower rise in ALS and an increase in rT3 compared to survivors (n10) in response to 5 days treatment with GHRP-2+TRH infusion. This was also reflected in the positive correlation between Apache II score and the change in rT3, and the inverse correlation between Apache II and the change in ALS, both parameters being inversely interrelated.

The responsiveness to 5 days GHRP-2+TRH infusion was not detectably different between survivors and non-survivors for the studied variables, except for the increase in ALS, which was lower in non-survivors (mean±SD of 25±21% versus 108±50%, P=0.009), the increase in rT3, which was higher in non-survivors (86±99% versus 5±423%, P=0.04), and IGFBP-1 levels which tended to increase in response to GHRP-2+TRH treatment only in the non-survivors (P=0.08) (FIG. 9).

Apache II score, calculated at time of study inclusion, was positively correlated with the increase in rT3z($R^2=0.48$, P=0.006) obtained after 5 days infusion of, GHRP-2+TRH and inversely related to the increase in ALS ($R^2=0.28$, P=0.04). The increase in rT3 and the increase in ALS after 5 days secretagogue infusion were inversely interrelated ($R^2=0.61$, P=0.001) (FIG. 9).

3. Discussion

The endocrine changes observed during the course of critical illness are thought to represent a variety of adaptive, beneficial responses. The current example provides evidence against this assumption, revealing that in protracted critically ill patients supported with intensive care for several weeks or months, the "wasting syndrome" is—at least in part—brought about by relatively insufficient release of anterior pituitary hormones, associated with reduced secretory activity of target organs. Hyperactivity of the pituitary-adrenocortical axis no longer seems to play a crucial role in the metabolic presentation of this particular wasting condition. Excessive protein degradation appears to be related specifically to the low activity status of the thyroid axis and to elevated circulating levels of IGFBP-1 whereas impaired synthesis of protein and low leptin levels despite feeding are linked to the impaired secretion of GH and to low circulating levels of IGF-1 and GH-dependent binding proteins. Continuous infusion of the GH-secretagogue GHRP-2 in combination with TRH for 5 days was found to reactivate the blunted GH and TSH secretion with preserved peripheral responsiveness and feedback inhibition and without affecting cortisol release. This novel endocrine strategy reduced protein degradation, evidenced by decreased urea production, while stimulating protein synthesis, indicated by a rise in the biochemical markers of anabolism in bone.

Reduced pulsatile GH secretion was related to low circulating levels of IGF-1, IGFBP-3 and ALS in protracted critical illness. Now low levels of IGFBP-5 are added to the spectrum of reduced somatotropism, a GH-controlled binding protein known to stimulate bone formation. The hyposomatotropism was linked to the lack of anabolism as indicated by biochemical markers such as OC and leptin.

Concomitantly, markers of hypercatabolism such as increased urea production and urinary excretion of collagen cross-links were related to relatively high IGFBP-1 concentrations and to the degree of tertiary hypothyroidism.

Within the short time of 5 days, combined and continuous infusion of GHRP-2 and TRH substantially altered the endocrine and metabolic presentation of protracted critical illness.

The inventors have also shown that infusion of GHRP-2 for 21 h in this condition increases pulsatile GH secretion >6-fold, associated with increases in IGF-I, IGFBP-3 and ALS. A 21 h infusion of TRH did not alter any of the GH-dependent parameters while increasing TSH secretion and thyroid hormone levels. Here, it was found that after 5 days infusion of GHRP-2+TRH, pulsatile GH secretion was still 3-fold higher compared to baseline and was positively related to serum levels of IGF-I and GH-dependent IGFBP'S, that had all reached normal or near-normal levels from day 2 onwards and were stable thereafter. This observation strongly favors the presence of active feedback inhibition preventing overcorrection of the somatotropic axis with this strategy. Treatment with high doses of recombinant human GH has recently shown to increase morbidity and mortality of critical illness. The inability to overtreat with GH-secretagogues is an important advantage over exogenous GH, especially in the vulnerable critically ill elderly.

Taking the fed state into account, baseline insulin levels were not substantially elevated—if at all—and they tended to further decrease during placebo infusion while IGFBP-1 levels increased. The illness—induced changes were both reversed by GHRP-2+TRH infusion.

GHRP-2+TRH infusion acutely increased circulating leptin levels which slightly declined subsequently. The initial leptin rise attributes this effect to the presence of the GH-secretagogue in the combined peptide infusion.

The rises in pulsatile GH secretion and in serum IGF-I, ALS, insulin and leptin levels were reversible within 5 days after interruption of the GHRP-2+TRH infusion. Compared to the pretreatment condition, there was no suppression of the somatotropic axis, excluding a major downregulation of the GH-secretagogue receptor. Circulating levels of IGFBP-3 and IGFBP-5 remained above the pretreatment value after 5 days of placebo following GHRP2+TRH.

The mean nocturnal TSH concentrations observed after 5 days infusion of GHRP-2+TRH were still elevated compared to baseline in the presence of increased and stable T4 and T3 levels, both approaching normal values. Again, this constellation favors active feed-back inhibition loops preventing overstimulation of the thyroid gland. The possibility of "individualized" peripheral hormonal responses to GHRP-2+TRH infusion may reflect an important safety aspect for an endocrine treatment at a time when it is difficult—if not impossible—to determine the optimal level of peripherally active hormones.

The endocrine changes evoked by infusion of GHRP-2+TRH for S days were associated with relevant metabolic alterations.

Urea production, increased at baseline, was found to drop substantially by infusing GHRP-2+TRH for 5 days, the effect being detectable within 2 days, sustained for the duration of the infusion and found to be reversible within a day after interruption of the treatment. A reduction of the urea production while nutritional intake is stable, as observed here, indicates limited degradation of protein, suggesting counteraction of the hypercatabolism. This effect was related to the correction of the low thyroid hormone levels and therefore refutes the assumption that low thyroid hormone levels are an adaptive mechanism to limit hypercatabolism in protracted critical illness.

Concomitantly, a significant increase of the low serum OC concentrations occurred, accompanied by a tendency towards a decrease—if anything—in the circulating levels of PICP and sALP. This constellation indicates increased bone formation selectively by activation of mature osteoblasts. In view of the observed positive correlation with the IGF(BP)-response, this anabolic effect is most likely mediated, either directly or indirectly, by the reactivation of the somatotropic axis (GH/bone). Moreover, this brief intervention was capable of restoring the positive correlation between OC and DPD, suggesting that communication between osteoblasts and osteoclasts was at least partially reinstalled. Indeed, normal coupling of bone formation and resorption is a dynamic and tightly regulated process involving local and systemic effects of the stimulatory IGFBP-3 and −5 and the inhibitory IGFBP-4. Increasing (systemic and eventually local) production of IGF-I together with IGFBP-3 and −5 in this condition without altering IGFBP-4 most likely explains the observed reactivation of bone formation. Interestingly, the only parameter found to relate both to OC levels and to DPD was serum leptin concentration. Since a stimulatory effect of leptin on osteoblast differentiation has recently been demonstrated in vitro, this finding may point towards a role for this hormone in the physiological coupling between bone resorption and formation. Finding DPD to be unaltered by GHRP-2+TRH treatment indicates that—at least within the short time frame of 5 days—the effect of this endocrine intervention does not primarily involve the osteoclast. Stimulation of bone formation in a clinical condition known to be complicated by osteoporosis and impaired healing of surgical or traumatic bone injury is likely to be beneficial.

Of all patients admitted to ICU'S, less then 20% will become "long-stay" patients as those studied here. This minority has a high mortality risk and requires a major part of the resources for intensive care medicine. A preliminary but remarkable finding in the current study was that a high IGFBP-1 concentration for age predicted unfavorable outcome, whereas the Apache II severity of illness score was unable to do so.

Insulin concentrations were lower in the non-survivors compared to the survivors for the same blood glucose level, which could explain the higher concentrations of IGFBP-1. Together these data indicate that impaired glucose metabolism or disposal rate, which cannot be delineated merely by measuring blood glucose levels in an individual patient, contributes to an unfavorable outcome. Moreover, documenting low instead of high insulin levels in the most severely ill patients also challenges the current recommendation to allow blood glucose levels to be substantially above the normal range in protracted critical illness, a strategy that had been extrapolated from the insulin-resistance documented in acute stress conditions.

In conclusion, the "wasting syndrome" of protracted critical illness is—at least in part—brought about by impaired pulsatile GH and TSH release and reduced secretory activity of the respective target organs. Increased catabolism was found to relate selectively to the degree of tertiary hypothyroidism whereas impaired anabolism was linked to hyposomatotropism. The continuous infusion of GHRP-2+TRH for 5 days jointly reactivated both axes, respected important feedback inhibition loops which avoided overtreatment and did not affect cortisol release. This novel endocrine strategy evoked a shift towards anabolic metabolism, as indicated by biochemical markers. Hereby the first evidence is provided of effectiveness of secretagogues for treatment of the "wasting syndrome" in protracted critical illness.

TABLE I

| randomization | age | gender | BMI | diagnosis | APACHE II adm |
|---|---|---|---|---|---|
| placebo/GHRP + TRH | 79.4 | M | 23.9 | complicated AA repair + respiratory failure | 15 |
| placebo/GHRP + TRH | 72.0 | M | 24.5 | necrotising pancreathis | 33 |
| placebo/GHRP + TRH | 62.6 | M | 38.1 | mediastinitis after esophageal resection | 7 |
| placebo/GHRP + TRH | 73.3 | M | 22.3 | redo CABG + candida sepsis | 9 |
| placebo/GHRP + TRH | 77.6 | F | 22.9 | mitral valve replacement + LCOS | 15 |
| placebo/GHRP + TRH | 73.2 | M | 19.0 | respiratory failure after lobectomia (sepsis) | 14 |
| GHRP + TRH/placebo | 52.4 | M | 24.0 | mediasilmitis after esophageal resection | 20 |
| GHRP + TRH/placebo | 80.8 | F | 29.4 | aortic valve replacement, CABG, LCOS | 18 |
| GHRP + TRH/placebo | 72.0 | M | 24.0 | fecal paritonitis | 18 |
| GHRP + TRH/placebo | 74.2 | F | 24.2 | respiratory failure after esophageal resection (sepsis) | 15 |
| GHRP + TRH/placebo | 53.3 | M | 24.6 | multiple trauma + quadruplegia – fecal paritonitis | 9 |
| GHRP + TRH/placebo | 77.2 | F | 19.0 | fecal paritonitis | 18 |
| GHRP + TRH/placebo | 84.9 | M | 22.9 | respiratory failure (pneumonia) after pneumonectomy | 19 |
| GHRP + TRH/placebo | 44.2 | M | 24.2 | multiple trauma, necrotising cholecystitis, endocarditis | 11 |

| randomization | APACHE II Incl | exog insul | feeding | Cal/kg/d | ICU stay at incl (d) | total ICU stay (d) | outcome |
|---|---|---|---|---|---|---|---|
| placebo/GHRP + TRH | 13 | n | BN | 31 | 75 | 110 | dead ICU |
| placebo/GHRP + TRH | 13 | y | TPN | 26 | 56 | 88 | home |
| placebo/GHRP + TRH | 12 | n | TPN | 23 | 18 | 54 | home |
| placebo/GHRP + TRH | 15 | y | TPN | 29 | 82 | 117 | home |
| placebo/GHRP + TRH | 10 | y | BN | 25 | 15 | 26 | home |
| placebo/GHRP + TRH | 9 | y | TPN | 33 | 82 | 119 | dead ICU |
| GHRP + TRH/placebo | 15 | y | TPN | 35 | 15 | 54 | home |
| GHRP + TRH/placebo | 21 | n | BN | 29 | 18 | 23 | dead ICU |
| GHRP + TRH/placebo | 14 | y | TPN | 27 | 14 | 38 | home |
| GHRP + TRH/placebo | 16 | n | PN + EN | 34 | 27 | 45 | home |
| GHRP + TRH/placebo | 8 | n | TPN | 26 | 39 | 70 | home |
| GHRP + TRH/placebo | 23 | y | TPN | 32 | 22 | 33 | dead ICU |
| GHRP + TRH/placebo | 16 | n | PN + EN | 33 | 22 | 41 | home |
| GHRP + TRH/placebo | 13 | y | PN + EN | 28 | 71 | 148 | home |

TABLE II

| | mean ± SD | median | P25–P75 | mean ± SD matched controls | normal range for assay | P vs. controls |
|---|---|---|---|---|---|---|
| age (y) | 68.4 ± 11.3 | 72.6 | 62.6–77.2 | | | |
| mean nocturnal GH ($\mu$g/L) | 1.04 ± 0.89 | 0.75 | 0.43–1.80 | | | |
| GH half-life (min) | 17.9 ± 3.4 | 17.9 | 15.8–21.0 | | 18 | |
| GH pulse amplitude ($\mu$g/Lv.min) | 0.104 ± 0.11 | 0.052 | 0.029–0.150 | | | |
| GH pulse mass ($\mu$g/Lv) | 3.02 ± 2.59 | 2.00 | 1.20–4.50 | | | |
| number of GH pulses from 21:00 h to 08:00 h | 4.9 ± 1.1 | 5.0 | 4.0–6.0 | | 3.0 | |
| nocturnal basal GH secretion ($\mu$g/Lv.min) | 0.013 ± 0.009 | 0.012 | 0.007–0.018 | | | |
| nocturnal pulsatile GH production ($\mu$g/Lv over 9 h) | 12.9 ± 8.5 | 9.9 | 6.3–18.0 | | | |
| IGF-I ($\mu$g/L) | 87 ± 32 | 74 | 58–109 | 130 ± 47 | 58–284 | 0.001 |
| IGFBP-3 (mg/L) | 1.41 ± 0.81 | 1.32 | 0.75–1.59 | | 2.20–4.60 | |
| ALS (mg/L) | 6.4 ± 3.3 | 5.4 | 4.2–7.1 | | 17.0–34.0 | |
| IGFBP-1 ($\mu$g/L) | 10.8 ± 6.5 | 9.4 | 4.9–15.8 | | 0.0–52.0 | |
| insulin ($\mu$U/mL) | 36 ± 36 | 22 | 15–37 | | | |
| luptin ($\mu$g/L) | 15.8 ± 13.1 | 10.8 | 4.8–28.1 | | | |
| mean nocturnal cortisol (nmol/L) | 424 ± 149 | 440 | 378–500 | | <50–276 | |
| mean nocturnal TSH (mIU/L) | 1.30 ± 1.33 | 0.89 | 0.34–1.90 | | 0.15–7.0 | |
| T4 (nmol/L) | 77 ± 25 | 78 | 60–94 | | 71–154 | |
| T3 (nmol/L) | 0.85 ± 0.24 | 0.80 | 0.70–1.02 | | 1.20–2.90 | |
| rT3 (nmol/L) | 1.01 ± 0.71 | 0.77 | 0.51–1.62 | | 0.30–0.80 | |
| mean nocturnal PRL ($\mu$g/L) | 13.1 ± 12.2 | 10.5 | 8.8–12.1 | | 9.0–30.0 | |
| IGFBP-4 ($\mu$g/L) | 877 ± 204 | 826 | 708–1074 | 607 ± 185 | 380–1295 | <0.0001 |
| IGFBP-5 ($\mu$g/L) | 379 ± 124 | 361 | 306–437 | 612 ± 119 | 322–1020 | <0.0001 |
| 25(OH)O3 ($\mu$g/L) | 10.6 ± 5.2 | 9.4 | 6.6–14.4 | 20.1 ± 9.0 | 7.0–60.0 | <0.0001 |
| bone-specific alkaline phosphatase ($\mu$g/L) | 13.5 ± 11.4 | 8.6 | 6.8–15.2 | 9.1 ± 5.4 | 9.0–15.0 | NS |
| osteocalcin ($\mu$g/L) | 29.5 ± 14.3 | 27.8 | 19.5–30.6 | 34.5 ± 29 | 13.2–254.0 | 0.04 |
| type I procollagen ($\mu$g/L) | 256 ± 108 | 219 | 184–288 | 51.4 ± 20.4 | 75–254 | <0.0001 |
| urinary pyridinoline/creatinine (nmol/mmol) | 836 ± 776 | 520 | 401–1030 | 81 ± 27 | 27–182 | <0.0001 |
| urinary deoxypyridinolone/creatinine (nmol/mmol) | 106 ± 80 | 99 | 49–122 | 12 ± 5 | 4.3–27.5 | <0.0001 |
| blood urea/creatinine ratio | 84 ± 39 | 73 | 64–89 | | 15–40 | |

What is claimed is:

1. A method of treating a patient afflicted with protein hypercatabolism, comprising administering by infusion to a subject suffering from said protein hypercatabolism an amount of Thyroid Releasing Hormone (TRH) and of Growth Hormone-Releasing Peptide (GHRP) effective to reactivate blunted anterior pituitary hormone release, for a time and under conditions effective to mitigate protein hypercatabolism.

2. The method according to claim 1, wherein GHRP is administered at a rate of between 0.01 and 10 $\mu$g per kg per hour to said subject and TRH is administered at a rate of between 0.01 and 10 µg per kg per hour to said subject.

3. The method as claimed in claim 1, wherein the weight ratio of GHRP to TRH is between 0.5 and 4.

4. The method as claimed in claim 3, wherein the weight ratio of GHRP to TRH is between 0.5 and 2.

5. A method for treating a patient afflicted with protein hypercatabolism comprising administering by infusion to a subject suffering from said protein hypercatabolism an amount of Thyroid Releasing Hormone (TRH) and of Growth Hormone-Releasing Peptide (GHRP) suitable to mitigate protein hypercatabolism in a patient afflicted with protein hypercatabolism.

6. The method as claimed in claim 5, wherein delivery of 0.01–10 µg Growth Hormone-Releasing Peptide per kg of the subject per hour and 0.01–10 µg Thyroid Releasing Hormone per kg of the subject per hour is thereby accomplished.

* * * * *

UNITED STATES PATENT AND TRADEMARK OFFICE
CERTIFICATE OF CORRECTION

PATENT NO. : 6,797,698 B1
DATED : September 28, 2004
INVENTOR(S) : Van Den Berghe Page 1 of 1

It is certified that error appears in the above-identified patent and that said Letters Patent is hereby corrected as shown below:

Title page,
Item [56], References Cited, OTHER PUBLICATIONS, first reference, "Practice of Parmacy" should read -- Practice of Pharmacy --

Column 1,
Line 24, "inventors were" should read -- inventor was --

Column 11,
Line 8, "IGFBP 3" should read -- IGFBP-3 --

Signed and Sealed this

Fifth Day of April, 2005

JON W. DUDAS
*Director of the United States Patent and Trademark Office*